United States Patent [19]

Harada et al.

[11] Patent Number: 5,792,883
[45] Date of Patent: Aug. 11, 1998

[54] PREPARATION OF DIARYL CARBONATE

[75] Inventors: Katsumasa Harada; Ryoji Sugise; Koichi Kashiwagi; Takashi Doi; Sadao Niida; Toshio Kurafuji, all of Yamaguchi, Japan

[73] Assignee: Ube Industries, Ltd., Yamaguchi, Japan

[21] Appl. No.: 944,251

[22] Filed: Oct. 6, 1997

[30] Foreign Application Priority Data

Oct. 4, 1996 [JP] Japan ............... 8-264765

[51] Int. Cl.$^6$ ............... C07C 68/00
[52] U.S. Cl. ............... 558/274; 558/271; 558/272; 558/273
[58] Field of Search ............... 558/274, 271, 558/272, 273

[56] References Cited

U.S. PATENT DOCUMENTS 4,544,507 10/1985 Foley .
5,648,510 7/1997 Harada et al. ............... 558/274

FOREIGN PATENT DOCUMENTS 0737665 10/1996 European Pat. Off. .
0 795 539 9/1997 European Pat. Off. ........ C07C 68/00

Primary Examiner—Michael G. Ambrose
Attorney, Agent, or Firm—McAulay Fisher Nissen Goldberg & Kiel, LLP

[57] ABSTRACT

An improved process for preparing a diaryl carbonate from a diaryl oxalate in a liquid phase by decarbonylation utilizes a reaction vessel composed of two or more reaction chambers which are connected in series. The process is composed of the steps of continuously introducing the diaryl oxalate and an organic phosphorus compound having a trivalent or pentavalent phosphorus atom and at least one carbon-phosphorus bonding into the first chamber and continuously recovering a reaction mixture mainly containing the diaryl carbonate from the last chamber under the condition that a mixture of the diaryl oxalate and the organic phosphorus compound is heated in the reaction chambers, while discharging carbon monoxide released from the mixture.

12 Claims, 1 Drawing Sheet

PREPARATION OF DIARYL CARBONATE

FIELD OF THE INVENTION

The present invention relates to a process for preparing a diaryl carbonate from a diaryl oxalate in a liquid phase by decarbonylation.

BACKGROUND OF THE INVENTION

It is known that a diaryl carbonate can be prepared from a diaryl oxalate by decarbonylation. The known process, however, is not favorably employable in industry because the reaction rate is very slow and the yield and selectivity are low.

Yuki Gosei Kagaku Kyokaishi (Journal of Synthetic Organic Chemistry, Japan), Vol.5, No.4–9, Report 47, pp. 70–71(1948) teaches a reaction in which diphenyl oxalate is heated to release carbon monoxide to give diphenyl carbonate. This report describes neither yield nor selectivity. According to a trace experiment of the experiment of this report, only a small amount of diphenyl carbonate is produced.

U.S. Pat. No. 4,544,507 describes that the carbonic acid dialkyl ester, i.e., dialkyl carbonate, can be prepared by heating a dialkyl oxalate in a liquid phase at 50°–150° C. in the presence of an alcolate catalyst. In the working example of the Patent publication, the diphenyl oxalate is heated in the presence of a potassium phenoxide catalyst only to give mainly the diphenyl oxalate, namely, the starting compound.

SUMMARY OF THE INVENTION

It is an object of the present invention to provide a new process for continuously preparing a diaryl carbonate from a diaryl oxalate by decarbonylation in an increased yield with a high selectivity.

The present invention resides in a process for preparing a diaryl carbonate from a diaryl oxalate in a liquid phase by decarbonylation which utilizes a reaction vessel comprising at least two reaction chambers connected in series and comprises the steps of continuously introducing the diaryl oxalate and a decarbonylation catalyst (typically, an organic phosphorus compound having a trivalent or pentavalent phosphorus atom and at least one carbon-phosphorus bonding) into the first chamber and continuously recovering a reaction mixture comprising the diaryl carbonate from the last chamber under the condition that a mixture of the diaryl oxalate and the organic phosphorus compound is heated in the reaction chambers, while discharging carbon monoxide released from the mixture.

BRIEF DESCRIPTION OF DRAWINGS

Each of FIGS. 1 to 3 illustrates a schematic view of a reaction vessel having a plural number of reaction chambers which is employable for performing the process of the invention.

DETAILED DESCRIPTION OF THE INVENTION

Figure 1:
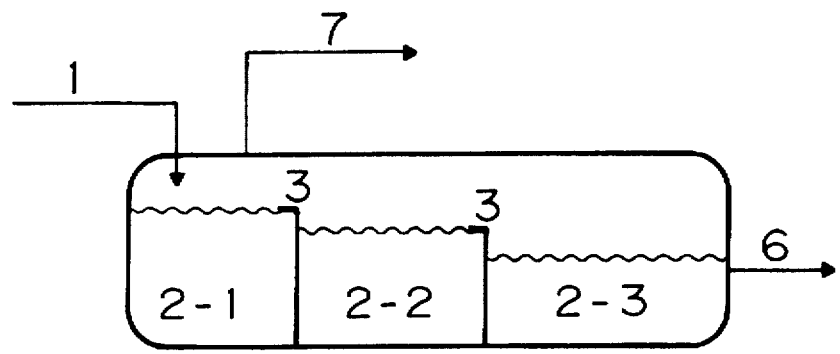

The decarbonylation process for preparing a diaryl carbonate from a diaryl oxalate can be illustrated as follows:

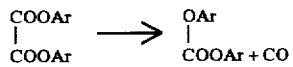

wherein Ar stands for an unsubstituted or substituted aryl group.

In the process of the invention, a reaction vessel comprising at least two reaction chambers which are connected in series is employed. In the process, a diaryl oxalate and a decarbonylation catalyst (typically, an organic phosphorus compound having a trivalent or pentavalent phosphorus atom and at least one carbon-phosphorus bonding) in a liquid state is continuously introduced into the first chamber. If one or more intermediate reaction chambers are placed in the reaction vessel, the reaction mixture of the diaryl oxalate and the decarbonylation catalyst is transferred from the first chamber into the intermediate reaction chambers in sequence, and finally the reaction mixture comprising the produced diaryl carbonate is continuously recovered from the last chamber. In the reaction chambers, the mixture of the diaryl oxalate and the decarbonylation catalyst is heated, while continuously or intermittently discharging carbon monoxide released from the mixture.

The aryl group of the diaryl oxalate can be: (1) a phenyl group; (2) a phenyl group having one or more substituents such as an alkyl group having 1 to 12 carbon atoms (e.g., methyl and ethyl), an alkoxy group having 1 to 12 carbon atoms (e.g., methoxy and ethoxy), a halogen atoms (e.g., fluorine and chlorine), and nitro; or (3) a naphthyl group. Preferred is a phenyl group.

The phenyl group having one or more substituents, that is named "a substituted phenyl group", may be in the form of one of various isomers. Examples of the isomers include 2-(or 3-, or 4-)alkylphenyl, such as 2-(or 3-, or 4-)methylphenyl, or 2-(or 3-, or 4-)ethylphenyl; 2-(or 3-, or 4-)alkoxyphenyl, such as 2-(or 3-, or 4-)-methoxyphenyl, or 2-(or 3-, or 4-)ethoxyphenyl; 2-(or 3-, or 4-)halogenated phenyl, such as 2-(or 3-, or 4-)fluorophenyl, or 2-(or 3-, or 4-)chlorophenyl; and 2-(or 3-, or 4-)nitrophenyl.

Examples of the diaryl oxalates include diphenyl oxalate, bis(2-methylphenyl) oxalate, bis(3-methylphenyl) oxalate, bis(4-methylphenyl) oxalate, bis(2-chlorophenyl) oxalate, bis(3-chlorophenyl) oxalate, bis(4-chlorophenyl) oxalate, bis(2-nitrophenyl) oxalate, bis(3-nitrophenyl) oxalate, and bis(4-nitrophenyl)oxalate. Most preferred is diphenyl oxalate.

In the decarbonylation process of the invention, the decarbonylation catalyst preferably is an organic phosphorus compound having a trivalent or pentavalent phosphorus atom, and having at least one carbon-phosphorus bonding. Preferred are organic phosphorus compounds having three or more carbon-phosphorus bondings. Preferred organic phosphorus compounds are a phosphonium salt having the following formula (A), a phosphine having the following formula (B), a phosphine dihalide having the following formula (C), and a phosphine oxide having the following formula (D):

Formula (A):

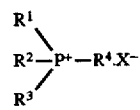

Formula (B):

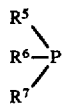

Formula (C):

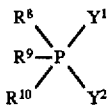

Formula (D):

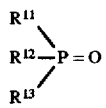

Detailed descriptions are given below for the phosphonium salt of formula (A), the phosphine of formula (B), the phosphine dihalide of formula (C), and the phosphine oxide of formula (D).

(A) Phosphonium Salt of the formula (A)

The phosphonium salt can be represented by the above formula (A), wherein each of $R^1$, $R^2$, $R^3$ and $R^4$ independently represents an aryl group of 6 to 10 carbon atoms, an alkyl group of 1 to 16 carbon atoms, an aralkyl group of 7 to 22 carbon atoms, an aryloxy group of 6 to 10 carbon atoms, or a heterocyclic group of 4 to 16 carbon atoms, and X represents a counter ion of the phosphonium ion. Any two of $R^1$, $R^2$, $R^3$ and $R^4$ may be combined to form a ring having the phosphorus atom as its ring member.

The aryl group is described in more detail. The aryl group can be a phenyl or naphthyl group. The phenyl or naphthyl group can have one or more substituents in any positions. Examples of the substituents include alkyl of 1 to 15 carbon atoms, preferably of 1 to 12 carbon atoms (e.g., methyl, ethyl, n-propyl, isopropyl, n-butyl, isobutyl, sec-butyl, or tert-butyl), alkoxy of 1 to 15 carbon atoms, preferably of 1 to 12 carbon atoms (e.g., methoxy, ethoxy, n-propoxy, isopropoxy, n-butoxy, isobutoxy, sec-butoxy, or tert-butoxy), alkoxycarbonyl of 2 to 12 carbon atoms, preferably of 2 to 8 carbon atoms (e.g., methoxycarbonyl or ethoxycarbonyl), aryl (e.g., phenyl), amino such as N,N-dialkyl-substituted amino (e.g., N,N-dimethylamino), cyano, nitro, and halo (e.g., fluoro, chloro, or bromo).

The alkyl group is described in more detail. The alkyl group can have 1 to 16 carbon atoms. Examples of the alkyl group include methyl, ethyl, n-propyl, isopropyl, n-butyl, isobutyl, sec-butyl, or tert-butyl. The alkyl group can have one or more substituents in any positions. Examples of the substituents are the same as those described for the substituents of the aryl group.

The aralkyl group is described in more detail. The aralkyl group can have 7 to 22 carbon atoms. Examples of the aralkyl group include benzyl, phenethyl and naphthylmethyl. The aralkyl group can have one or more substituents in any positions. Examples of the substituents are the same as those described for the substituents of the aryl group.

The aryloxy group is described in more detail. The aryloxy group can be a phenoxy or naphthoxy group. The aryloxy group can have one or more substituents in any positions. Examples of the substituents are the same as those described for the substituents of the aryl group.

The heterocyclic group is described in more detail. The heterocyclic group can have 4 to 16 carbon atoms, and at least one hetero atom such as oxygen, sulfur, or nitrogen. Examples of the heterocyclic group include thienyl, furyl, and pyridyl. The heterocyclic group can have one or more substituents in any positions. Examples of the substituents are the same as those described for the substituents of the aryl group.

The groups of $R^1$, $R^2$, $R^3$ and $R^4$ of the phosphonium salt can be the same or different from each other. For instance, all of the groups of $R^1$, $R^2$, $R^3$ and $R^4$ are aryl groups in one phosphonium salt, that is, a tetraarylphosphonium salt. Three of the groups are aryl groups and other one is another group, that is, a triarylphosphonium salt. Two of the groups are aryl groups and other two are other groups, that is, a diarylphosphonium salt. Only one of the groups is an aryl group and other three are other groups, that is, an arylphosphonium salt. All of the groups of $R^1$, $R^2$, $R^3$ and $R^4$ are other than the aryl groups. Preferred are the tetraarylphosphonium salt and an arylphosphonium salt in which three of the groups of $R^1$, $R^2$, $R^3$ and $R^4$ are aryl groups and other one is a heterocyclic group.

The counter ion ($X^-$) can be a halide ion (e.g., chloride ion, bromide ion, or iodide ion), a hydrogen dihalide ion (e.g., hydrogen dichloride ion, hydrogen dibromide ion, hydrogen diiodide ion, or hydrogen bromide chloride ion), a halogen acid ion (e.g., chlorate ion, bromate ion, or iodate ion), a per-halogen acid ion (e.g., perchlorate ion, perbromate ion, or periodate ion), an aliphatic carboxylate ion (e.g., acetate ion, trifluoroacetate ion, or propionate ion), an aromatic carboxylate ion (e.g., benzoate ion, or α- or β-naphthalenecarboxylate ion), an aromatic hydroxyl ion (e.g., phenoxide ion), an inorganic acid ion (e.g., sulfate ion, sulfite ion, phosphate ion, phosphite ion, borate ion, hydrogenborate ion, cyanate ion, thiocyanate ion, or fluoroborate ion), an alkylsulfonate or alkylsulfinate ion having an alkyl group of 1 to 16 carbon atoms (e.g., methyl, ethyl, n-propyl, or isopropyl), an arylsulfonate or arylsulfinate ion having an aryl group (e.g., phenyl, p-tolyl, or p-nitrophenyl), a tetraalkylborate ion having an alkyl group of 1 to 10 carbon atoms (e.g., tetramethylborate ion, or tetraethylborate ion), or a tetraarylborate ion (e.g., tetraphenylborate ion, or tetrakis-p-fluorophenylborate ion). Examples of preferred counter ions ($X^-$) include halide ions such as chloride ion, bromide ion and iodide ion, and hydrogen dihalide ions such as hydrogen dichloride ion, hydrogen dibromide ion, hydrogen diiodide ion, and hydrogen bromide chloride ion. Most preferred are chloride ion and hydrogen dichloride ion.

Concrete examples of the preferred phosphonium salts of the formula (A) are described below.

(1) Phosphonium salt in which all of $R^1$, $R^2$, $R^3$ and $R^4$ are aryl groups and $X^-$ is a halide ion Examples are tetraphenylphosphonium chloride, tetraphenylphosphonium bromide, tetraphenylphosphonium iodide, tetrakis(p-chlorophenyl)phosphonium chloride, tetrakis(p-fluorophenyl)phosphonium chloride, tetrakis(p-tolyl)phosphonium chloride, p-chlorophenyltriphenylphosphonium chloride, p-chlorophenyltriphenylphosphonium bromide, p-chlorophenyltriphenylphosphonium iodide, p-tolyltriphenylphosphonium chloride, p-tolyltriphenylphosphonium bromide, p-tolyltriphenylphosphonium iodide, m-trifluoromethylphenyltriphenylphosphonium chloride, p-biphenyltriphenylphosphonium chloride, m-methoxyphenyltriphenylphosphonium chloride, p-methoxyphenyltriphenylphosphonium chloride, p-ethoxyphenyltriphenylphosphonium chloride, p-ethoxyphenyltriphenylphosphonium bromide, p-ethoxyphenyltriphenylphosphonium iodide, p-dimethylaminophenyltriphenylphosphonium chloride, p-ethoxycarbonylphenyltriphenylphosphonium chloride, m-cyanophenyltriphenylphosphonium chloride, and 1-naphthyltriphenylphosphonium chloride. Most preferred is tetraphenylphosphonium chloride.

(2) Phosphonium salt in which all of $R^1$, $R^2$, $R^3$ and $R^4$ are aryl groups and $X^-$ is a hydrogen dihalide ion Examples are tetraphenylphosphonium hydrogen dichloride, tetraphenylphosphonium hydrogen dibromide, tetraphenylphosphonium hydrogen diiodide, and tetraphenylphosphonium hydrogen bromide chloride. Most preferred is tetraphenylphosphonium hydrogen dichloride.

(3) Phosphonium salt in which all of $R^1$, $R^2$, $R^3$ and $R^4$ are aryl groups and $X^-$ is an aliphatic or aromatic carboxylate ion Examples are tetraphenylphosphonium acetate, p-chlorophenyltriphenylphosphonium acetate, p-ethoxyphenyltriphenylphosphonium acetate, p-tolyltriphenylphosphonium acetate, tetraphenylphosphonium trifluoroacetate, and tetraphenylphosphonium benzoate.

(4) Phosphonium salt in which all of $R^1$, $R^2$, $R^3$ and $R^4$ are aryl groups and $X^-$ is fluoroborate ion Examples are tetraphenylphosphonium fluoroborate, p-chlorophenyltriphenylphosphonium fluoroborate, p-ethoxyphenyltriphenylphosphonium fluoroborate, and p-tolyltriphenylphosphonium fluoroborate.

(5) Phosphonium salt in which all of $R^1$, $R^2$, $R^3$ and $R^4$ are aryl groups and $X^-$ is thiocyanide ion An example is tetraphenylphosphonium thiocyanide.

(6) Phosphonium salt in which all of $R^1$, $R^2$, $R^3$ and $R^4$ are aryl groups and $X^-$ is an aromatic hydroxyl ion An example is tetraphenylphosphonium phenoxide.

(7) Phosphonium salt in which three of $R^1$, $R^2$, $R^3$ and $R^4$ are aryl groups, one is an alkyl group, and $X^-$ is a halide ion Examples are methyltriphenylphosphonium chloride, methyltriphenylphosphonium bromide, methyltriphenylphosphonium iodide, ethyltriphenylphosphonium chloride, ethyltriphenylphosphonium bromide, ethyltriphenylphosphonium iodide, n-propyltriphenylphosphonium chloride, n-propyltriphenylphosphonium bromide, n-propyltriphenylphosphonium iodide, isopropyltriphenylphosphonium chloride, isopropyltriphenylphosphonium bromide, n-dodecyltriphenylphosphonium chloride, n-dodecyltriphenylphosphonium bromide, chloromethyltriphenylphosphonium chloride, methyltris(m-chlorophenyl)phosphonium chloride, methyltris(m-chlorophenyl)phosphonium bromide, ethyltris(m-chlorophenyl)phosphonium chloride, and ethyltris(m-chlorophenyl)phosphonium bromide.

(8) Phosphonium salt in which three of $R^1$, $R^2$, $R^3$ and $R^4$ are aryl groups, one is an aralkyl group, and $X^-$ is a halide ion Examples are benzyltriphenylphosphonium chloride, p-fluorobenzyltriphenylphosphonium chloride, p-fluorobenzyltriphenylphosphonium bromide, 2,4-dichlorobenzyltriphenylphosphonium chloride, 2,4-dichlorobenzyltriphenylphosphonium bromide, p-n-butoxybenzyltriphenylphosphonium chloride, p-n-butoxybenzyltriphenylphosphonium bromide, 2-naphthylmethyltriphenylphosphonium chloride, 2-naphthylmethyltriphenylphosphonium bromide, 9-fluorenyltriphenylphosphonium chloride, and 9-fluorenyltriphenylphosphonium bromide.

(9) Phosphonium salt in which three of $R^1$, $R^2$, $R^3$ and $R^4$ are aryl groups, one is a heterocyclic group, and $X^-$ is a halide ion An example is 2-thiophenetriphenylphosphonium chloride.

(10) Phosphonium salt in which three of $R^1$, $R^2$, $R^3$ and $R^4$ are aryl groups, one is an aryloxy group, and $X^-$ is a halide ion An example is phenoxytriphenylphosphonium chloride.

(11) Phosphonium salt in which three of $R^1$, $R^2$, $R^3$ and $R^4$ are aryl groups, one is an alkyl group, and $X^-$ is an aliphatic carboxylate ion Examples are methyltriphenylphosphonium acetate, ethyltriphenylphosphonium acetate, and n-propyltriphenylphosphonium acetate.

(12) Phosphonium salt in which three of $R^1$, $R^2$, $R^3$ and $R^4$ are aryl groups, one is an alkyl group, and $X^-$ is a fluoroborate ion Examples are methyltriphenylphosphonium fluoroborate, ethyltriphenylphosphonium fluoroborate, and n-propyltriphenylphosphonium fluoroborate.

(13) Phosphonium salt in which two of $R_1$, $R^2$, $R^3$ and $R^4$ are aryl groups, other two are other groups, and $X^-$ is a halide ion Examples are dimethyldiphenylphosphonium chloride, diethyldiphenylphosphonium chloride, dimethyldiphenylphosphonium bromide, and diethyldiphenylphosphonium bromide.

(14) Phosphonium salt in which one of $R^1$, $R^2$, $R^3$ and $R^4$ are aryl groups, other three are other groups, and $X^-$ is a halide ion Examples are diethylmethylphenylphosphonium chloride, and diethylmethylphenylphosphonium bromide.

(15) Phosphonium salt in which none of $R_1$, $R^2$, $R^3$ and $R^4$ are aryl groups, and $X^-$ is a halide ion Examples are tetra-n-butylphosphonium chloride, and tetra-n-butylphosphonium bromide.

Some of the above-mentioned phosphonium salts are known and available on market. Other phosphonium salts can be prepared by the processes set forth in Bull. Chem. Soc. Jpn., 56, 2869 (1983) and J. Am. Chem. Soc., 70, 737 (1948), or processes similar to those described in these publications.

For instance, the tetraarylphosphonium chloride can be prepared by reacting a triarylphosphine and an aryl halide (e.g., aryl iodide or aryl bromine) in the presence of a palladium acetate catalyst and treating the resulting tetraarylphosphonium iodide or bromide with an ion exchange resin (chloride type) to give the desired tetraarylphosphonium chloride. The produced tetraarylphosphonium chloride is preferably dried. For the drying, the tetraarylphosphonium chloride is preferably heated to 100° to 200° C. for 0.5 to 5 hours in a stream of a dry inert gas such as dry argon gas and then heated to 80° to 200° C. for 0.5 to 2 hours in a stream of a dry hydrogen chloride gas. The commercially available tetraarylphosphonium chloride is also preferred to be subjected to the above-mentioned process.

The tetraarylphosphonium salt having a counter ion other than halide ion can be prepared by reacting the above-obtained tetraarylphosphonium chloride with an alkali metal salt (e.g., sodium salt or potassium salt) or an ammonium salt of the desired counter ion, that is, ion exchange reaction. Other phosphonium salts other than the tetraaryl phosphonium salts can be prepared in the same manner or an analogous manner. These phosphonium salts are also preferred to be subjected to the drying treatment, in advance of its use as the catalyst.

(B) Phosphine of the formula (B)

The phosphine can be represented by the above formula (B), wherein each of $R^5$, $R^6$ and $R^7$ independently represents an aryl group, an alkyl group of 1 to 16 carbon atoms, an aralkyl group of 7 to 22 carbon atoms, or a heterocyclic group of 4 to 16 carbon atoms. Any two of $R^5$, $R^6$ and $R^7$ may be combined to form a ring having the phosphorus atom as its ring member.

Examples of the aryl group, alkyl group, aralkyl group and heterocyclic group are the same as those described for the phosphonium salt of the formula (A).

The groups of $R^5$, $R^6$ and $R^7$ of the phosphine can be the same or different from each other. For instance, all of the groups of $R^5$, $R^6$ and $R^7$ are aryl groups in one phosphine, that is, a triarylphosphine. Two of the groups are aryl groups and other one is another group, that is, a diarylphosphine. Only one of the groups is an aryl group and other two are other groups, that is, an arylphosphine. All of the groups of $R^5$, $R^6$ and $R^7$ are other than the aryl groups. Preferred is the phosphine in which all of the groups of $R^5$, $R^6$ and $R^7$ are aryl groups.

Concrete examples of the preferred phosphines of the formula (B) are described below.

(1) Phosphine in which all of $R^5$, $R^6$ and $R^7$ are aryl groups (i.e., triarylphosphine)

Examples are triphenylphosphine, tris(p-chlorophenyl) phosphine, tris(p-tolyl)phosphine, and α-naphthyl(phenyl)-p-methoxyphenylphosphine.

(2) Phosphine in which two of $R^5$, $R^6$ and $R^7$ are aryl groups and one is other group (i.e., diarylphosphine)

Examples are methyldiphenylphosphine and phenyl-(p-methoxyphenyl)methylphosphine.

(3) Phosphine in which one of $R^5$, $R^6$ and $R^7$ is an aryl group and other two are other groups (i.e., arylphosphine)

Examples are dimethyl(phenyl)phosphine and ethyl (phenyl)-n-propylphosphine.

(4) Phosphine in which none of $R^5$, $R^6$ and $R^7$ are aryl groups

Examples are benzyl-(n-butyl)methylphosphine and tributylphosphine. An example of a phosphine in which any two of $R^5$, $R^6$ and $R^7$ are combined to form a ring having the phosphorus atom as its ring member is phenylbiphenylenephosphine.

(C) Phosphine Dihalide of the formula (C)

The phosphine dihalide can be represented by the above formula (C), wherein each of $R^8$, $R^9$ and $R^{10}$ independently represents an aryl group, an alkyl group of 1 to 16 carbon atoms, an aralkyl group of 7 to 22 carbon atoms, or a heterocyclic group of 4 to 16 carbon atoms, and each of $Y^1$ and $Y^2$ independently represents a halogen atom such as chlorine, bromine or iodine. Any two of $R^8$, $R^9$ and $R^{10}$ may be combined to form a ring having the phosphorus atom as its ring member.

Examples of the aryl group, alkyl group, aralkyl group and heterocyclic group are the same as those described for the phosphonium salt of the formula (A).

The groups of $R^8$, $R^9$ and $R^{10}$ of the phosphine dihalide can be the same or different from each other. For instance, all of the groups of $R^8$, $R^9$ and $R^{10}$ are aryl groups in one phosphine, that is, a triarylphosphine dihalide. Two of the groups are aryl groups and other one is another group, that is, a diarylphosphine dihalide. Only one of the groups is an aryl group and other two are other groups, that is, an arylphosphine dihalide. All of the groups of $R^8$, $R^9$ and $R^{10}$ are other than the aryl groups. Preferred is the phosphine dihalide in which all of the groups of $R^8$, $R^9$ and $R^{10}$ are aryl groups.

Concrete examples of the preferred phosphine dihalides of the formula (C) are triphenylphosphine dichloride, triphenylphosphine dibromide, and triphenylphosphine diiodide.

(D) Phosphine Oxide of the formula (D)

The phosphine oxide can be represented by the above formula (D), wherein each of $R^{11}$, $R^{12}$ and $R^{13}$ independently represents an aryl group, an alkyl group of 1 to 16 carbon atoms, an aralkyl group of 7 to 22 carbon atoms, or a heterocyclic group of 4 to 16 carbon atoms. Any two of $R^{11}$, $R^{12}$ and $R^{13}$ may be combined to form a ring having the phosphorus atom as its ring member.

Examples of the aryl group, alkyl group, aralkyl group and heterocyclic group are the same as those described for the phosphonium salt of the formula (A).

The groups of $R^{11}$, $R^{12}$ and $R^{13}$ of the phosphine oxide can be the same or different from each other. For instance, all of the groups of $R^{11}$, $R^{12}$ and $R^{13}$ are aryl groups in one phosphine, that is, a triarylphosphine oxide. Two of the groups are aryl groups and other one is another group, that is, a diarylphosphine oxide. Only one of the groups is an aryl group and other two are other groups, that is, an arylphosphine oxide. All of the groups of $R^{11}$, $R^{12}$ and $R^{13}$ are other than the aryl groups. Preferred is the phosphine oxide in which all of the groups of $R^{11}$, $R^{12}$ and $R^{13}$ are aryl groups.

Concrete examples of the preferred phosphine oxides of the formula (D) are described below.

(1) Phosphine oxide in which all of $R^{11}$, $R^{12}$ and $R^{13}$ are aryl groups (i.e., triarylphosphine oxide)

Examples are triphenylphosphine oxide, tris(p-chlorophenyl)phosphine oxide, tris(p-tolyl)phosphine oxide, and α-naphthyl (phenyl)-p-methoxyphenylphosphine oxide.

(2) Phosphine oxide in which two of $R^{11}$, $R^{12}$ and $R^{13}$ are aryl groups and one is other group (i.e., diarylphosphine oxide)

Examples are methyldiphenylphosphine oxide and phenyl-(p-methoxyphenyl)methylphosphine oxide.

(3) Phosphine oxide in which one of $R^{11}$, $R^{12}$ and $R^{13}$ is an aryl group and other two are other groups (i.e., aryl phosphine oxide)

Examples are dimethyl(phenyl)phosphine oxide and ethyl (phenyl) n-propylphosphine oxide.

(4) Phosphine oxide in which none of $R^{11}$, $R^{12}$ and $R^{13}$ are aryl groups Examples are benzyl-(n-butyl)methylphosphine oxide and tributylphosphine oxide. An example of a phosphine in which any two of $R^{11}$, $R^{12}$ and $R^{13}$ are combined to form a ring having the phosphorus atom as its ring member is phenylbiphenylenephosphine oxide.

Among the above-mentioned organic phosphorus compounds, tetraarylphosphonium halide, tetraarylphosphonium hydrogen dihalide, and triarylphosphine dihalide are preferred. Most preferred are tetraarylphosphonium chloride, tetraarylphosphonium hydrogen dichloride, and triarylphosphine dichloride. The organic phosphorus compound can be employed singly or in combination in the process of the present invention. The organic phosphorus compound can be dissolved or dispersed in the reaction medium.

The organic phosphorus compound can be employed in an amount of 0.001 to 50 mol. %, preferably 0.01 to 20 mol. %, based on the amount of diaryl oxalate (100 mol. %).

In the reaction for preparing a diaryl carbonate from a diaryl oxalate according to the invention, a halogen atom-containing compound can be incorporated. Particularly, in the cases where a phosphonium salt other than the phosphonium halide and phosphonium hydrogen dihalide are used as the phosphorus compound and where a phosphonium halide or a phosphonium hydrogen dihalide is used in a small amount, the incorporation of a halogen atom-containing compound is preferred. The halogen atom-containing compound preferably is a chlorine atom-containing compound or a bromine atom-containing compound. Most preferred is a chlorine atom-containing compound. The incorporated halogen atom-containing compound can be decomposed or converted into other halogen atom-containing compound in the course of the development of the reaction. The halogen atom-containing compound is generally employed in an amount of 0.001 to 300 moles, preferably 0.1 to 100 moles per one mole of the organic phosphorus compound.

The halogen atom-containing compound may be an inorganic compound or an organic compound.

Examples of the inorganic halogen atom-containing compounds are halides of aluminum (e.g., aluminum chloride and aluminum bromide), halides of metals belonging to the platinum group (e.g., platinum chloride, ruthenium chloride, palladium chloride, and chloroplatinic acid), halides of phosphorus (e.g., phosphorus trichloride, phosphorus pentachloride, phosphorus oxychloride, phosphorus tribromide, phosphorus pentabromide, and phosphorus oxybromide), hydrogen halides (e.g., hydrogen chloride and hydrogen bromide), halides of sulfur (e.g., thionyl chloride, sulfuryl chloride, sulfur dichloride, and disulfur dichloride), and halogens per se (e.g., chlorine and bromine).

The organic halogen atom-containing compound preferably contains (1) carbon atom, (2) a halogen atom such as chlorine atom or a bromine atom, and (3) at least one of other atoms selected from a hydrogen atom, a nitrogen atom, a sulfur atom, and a silicon atom.

Examples of the organic halogen atom-containing compounds are organic compounds having a C—Hal bonding (in which Hal means a halogen atom), a C—Si—Hal bonding, a C(O)—Hal bonding or a C—S(O)$_2$—Hal bonding. The organic halogen atom-containing compound can contain one or more halogen atoms such as chlorine(s), bromine(s) or iodine(s) singly or in combination.

Examples of the organic compounds having a C—Hal bonding include alkyl halides (e.g., chloroform, carbon tetrachloride, 1,2-dichloroethane, butyl chloride, and dodecyl chloride), aralkyl halides (e.g., benzyl chloride, benzotrichloride, triphenylmethyl chloride, and α-bromo-o-xylene), and halogenated aliphatic nitrites (e.g., β-chloropropionitrile, and γ-chlorobutyronitrile), halogenated aliphatic carboxylic acids (e.g., chloroacetic acid, bromoacetic acid, and chloropropionic acid).

Examples of the organic compounds having a C—Si—Hal bonding include halogenated silanes (e.g., diphenyldichlorosilane, and triphenylchlorosilane).

Examples of the organic compounds having a C(O)—Hal bonding include acyl halides (e.g., acetyl chloride, oxalyl chloride, propionyl chloride, stearoyl chloride, benzoyl chloride, 2-naphthalenecarboxylic acid chloride, and 2-thiophenecarboxylic acid chloride), halogenated formic acid aryl esters (e.g., phenyl chloroformate), and halogenated glyoxylic acid aryl esters (e.g., phenyl chloroglyoxylate).

Examples of the organic compounds having a C—S(O)$_2$—Hal bonding include sulfonyl chlorides (e.g., p-toluenesulfonic acid chloride, and 2-naphthalenesulfonic acid chloride).

The reaction for releasing CO from the diaryl oxalate according to the invention can be conducted at a temperature in the range of 100° to 450° C., preferably 160° to 450° C., more preferably 180° to 400° C., most preferably 180° to 350° C., in the reaction vessel comprising plural reaction chambers in the presence of the organic phosphorus compound, and optionally in combination with the halogen atom-containing compound. In the course of progress of the reaction, carbon monoxide is emitted and the desired diaryl carbonate is formed. The reaction can be conducted under an atmospheric pressure, under a certain pressure, or under a reduced pressure. If the reaction temperature is higher than the reflux temperature of the starting diaryl oxalate, the reaction is preferably performed under pressure.

The decarbonylation reaction does not require any solvent. However, if necessary, an organic solvent which does not participate in the reaction can be employed. Such solvent can be diphenyl ether, sulforane, N-methylpyrrolidone, dimethylimidazolidone, or 1,3-dimethyl 3,4,5,6-tetrahydro-2(1H)-pyrimidinone.

The reaction vessel comprising plural reaction chambers and the process for preparing a diaryl carbonate from a diaryl oxalate using the reaction vessel is now described in more detail.

FIG. 1 schematically illustrates one example of the reaction vessel which is employable for performing the reaction for preparing a diaryl carbonate from a diaryl oxalate according to the invention. In FIG. 1, a mixture of a diaryl oxalate and a decarbonylation catalyst is continuously supplied through a line 1 into the reaction vessel comprising three reaction chambers, 2-1, 2-2, 2-3. The reaction chambers are separated from each other by a partition 3. The partitions have heights differing from each other. The partition between the first chamber and the second chamber is higher than the partition between the second chamber and the third chamber, so that the reaction mixture is transferred in one direction, that is, from the first chamber to the second chamber and then to the third chamber. The upper spaces of the chambers are kept vacant to receive carbon monoxide which is produced in the course that the decarbonylation reaction proceeds. The mixture is first introduced into the first chamber 2-1 for performing the decarbonylation reaction by heating the mixture in the chamber 2-1, and the reaction mixture is then transferred into the second chamber 2-2 over the partition 3. The reaction mixture is heated in the second chamber 2-2 for advancing the decarbonylation reaction, and then transferred into the third chamber 2-3 over the partition 3. The reaction mixture received in the third chamber 3 is further heated to further advance the decarbonylation reaction. The reaction mixture thus enriched with the produced diaryl carbonate is finally recovered from the recovery line 6. In the course of the decarbonylation reaction, carbon monoxide is produced and discharged through a discharge line 7. The discharge line 7 may have a condenser (not illustrated).

There are no limitation with respect to the number of reaction chambers, but generally the reaction vessel comprises 2 to 30 reaction chambers, preferably 2 to 10 reaction chambers. There are no specific limitations with respect to the material of the reaction vessel. Ordinary reaction vessels such as vessels of glass or stainless (SUS) can be employed.

Figure 2:
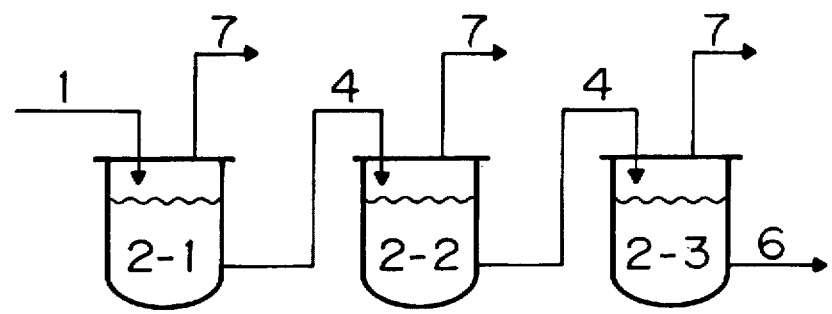

FIG. 2 schematically illustrates another example of the reaction vessel which is also employable for performing the reaction for preparing a diaryl carbonate according to the invention. In FIG. 2, a mixture of a diaryl oxalate and a decarbonylation catalyst is continuously supplied through a line 1 into the reaction chamber 2-1 which is in the form of an independent reaction vessel. The reaction chamber 2-1 is equipped with a line 4 for transferring the reaction mixture into the second chamber 2-2 which is also in the form of an independent reaction vessel. The reaction chamber 2-1 is further equipped with a carbon monoxide discharge line 7. The reaction mixture in the reaction chamber 2-1 is then transferred into the reaction chamber 2-2 of the same type through the line 4. The reaction mixture in the reaction chamber 2-2 is furthermore transferred into the reaction chamber 2-3 of the same type through the line 4. Finally, the reaction mixture enriched with the produced diaryl carbonate is recovered from the reaction chamber 2-3 through the line 6.

Figure 3:
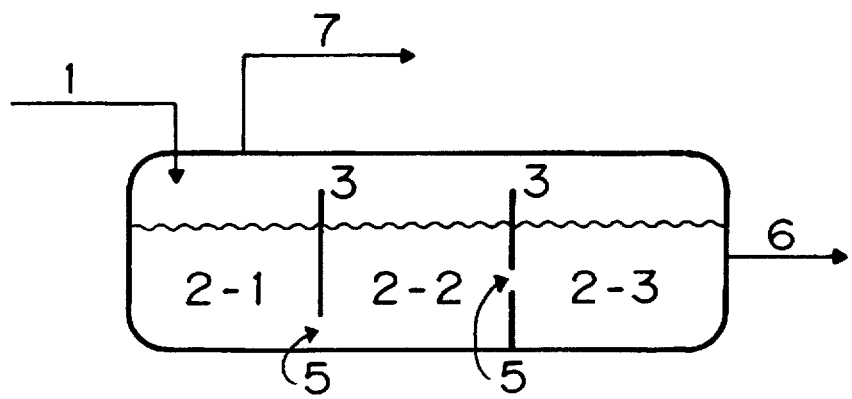

FIG. 3 schematically illustrates a further example of the reaction vessel which is a variation of the reaction vessel of FIG. 1 and is also employable for performing the reaction for preparing a diaryl carbonate according to the invention. The partitions 3 of the reaction vessel in FIG. 3 have the same height, but each has an opening 5 to assist the flow of the reaction mixture into the next chamber. The partition can be replaced with a partition having a plural number of small openings or a porous partition plate.

In the reaction chambers, a stirrer, a pump for circulation of the reaction mixture, or a gas blowing apparatus can be placed for well mixing the reaction mixture. Around the reaction chambers, a heater jacket can be placed to heat the reaction mixture in the chambers.

The reaction mixture recovered from the third (i.e., last) reaction chamber is subjected to a purification process such as distillation for isolating the produced diaryl carbonate in a high purity.

The residue produced in the distillation process comprises the catalyst, the unreacted diaryl oxalate, and the diaryl carbonate is again supplied into the first reaction chamber 2-1 after the diaryl oxalate, the decarbonylation catalyst, and optionally a halogen-containing compound are supplemented.

The carbon monoxide discharged from the reaction chambers is collected after trapping a volatile product in the condenser and can be employed for the preparation of a dialkyl oxalate which is utilized for the preparation of the diaryl oxalate.

The present invention is further described by the following examples. In the examples, the "conversion ratio of diaryl oxalate" (i.e., ratio of amount of consumed (or reacted) diaryl oxalate per the amount of charged diaryl oxalate) and "selectivity to diaryl carbonate" (i.e., ratio of the amount of produced diaryl carbonate per the amount of consumed diaryl oxalate) for decarbonylation reaction of the diaryl oxalate are all expressed in terms of molar percent ratio (i.e., mol. %). The rate of production of diaryl carbonate is expressed in terms of "g" of the diaryl carbonate produced in one hour in one liter of the reaction vessel.

Example 1

A reaction vessel illustrated in FIG. 1 was employed for performing the decarbonylation reaction of diphenyl oxalate to give diphenyl carbonate. The reaction vessel was composed of three chambers, 2-1, 2-2, and 2-3, each of which had a solution-receiving volume of 37 mL, 36 mL, and 48 mL, respectively. Therefore, the total volume (volume for receiving the reaction mixture) of the reaction vessel was 121 mL. The partitions were made of a non-porous glass plate. The reaction was performed in a stream of argon gas.

A mixture of diphenyl oxalate, tetraphenylphosphonium chloride ($PPh_4 \cdot Cl$) and chloroform was heated in a flask to 150° C. for give a liquid mixture in which $PPh_4 \cdot Cl$ was contained in 0.50 molar % and chloroform was contained in an amount of 6,400 ppm. The liquid mixture was continuously introduced at a rate of 27 g/ hr., into the first chamber of the reaction vessel which was heated in an oil bath kept to 270° C.

The reaction mixture flowed from the reaction chamber 2-1 into the reaction chamber 2-2 over the partition 3, and then into the reaction chamber 2-3 over the partition 3. The reaction mixture in the reaction chamber 2-3 was continuously recovered from the line 6. The carbon monoxide produced in the course of the progress of reaction was discharged continuously through the discharge line 7. The lines for introducing the mixture of diphenyl oxalate and the catalyst and recovering the reaction mixture were heated to 150° C. The reaction mixture was stirred in each reaction chamber.

When the reaction reached the steady state, the reaction mixture recovered from the reaction chamber 2-3 was analyzed by gas chromatography to indicate that the reaction mixture comprised 93.0 wt. % of diphenyl carbonate and 6.1 wt. % of diphenyl oxalate. Therefore, the conversion ratio of diaryl oxalate was 94.6%, and the selectivity to diphenyl carbonate was 99.1%. The reaction rate (in terms of STY) for producing diaryl carbonate was 185 g/L·hr. The reaction temperatures were 250° C. in the chamber 2-1, 246° C. in the chamber 2-2, and 246° C. in the chamber 2-3.

Example 2

A reaction apparatus illustrated in FIG. 2 was employed for performing the decarbonylation reaction of diphenyl oxalate to give diphenyl carbonate. The reaction apparatus was composed of three 70 mL-volume reaction vessels, 2-1, 2-2, and 2-3. The reaction was performed in a stream of argon gas.

A mixture of diphenyl oxalate, tetraphenylphosphonium chloride ($PPh_4 \cdot Cl$) and chloroform was heated in a flask to 150° C. for give a liquid mixture in which $PPh_4 \cdot Cl$ was contained in 0.50 molar % and chloroform was contained in an amount of 6,500 ppm. The liquid mixture was continuously introduced at a rate of 34 g/ hr., into the first vessel 2-1 which was heated in an oil bath kept to 270° C.

When the amount of the reaction mixture in the vessel 2-1 reached 50 mL, the reaction mixture was transferred to the vessel 2-2. Then, when the amount of the reaction mixture in the vessel 2-2 reached 50 mL, the reaction mixture was transferred to the vessel 2-3. The reaction mixture in the vessel 2-3 was continuously recovered from the line 6. The carbon monoxide produced in the course of the progress of reaction was discharged continuously through the discharge lines 7. The lines for introducing the mixture of diphenyl oxalate and the catalyst and recovering the reaction mixture were kept at 150° C. The reaction mixture was stirred in each reaction vessel.

When the reaction reached the steady state, the reaction mixture recovered from the reaction vessel 2-3 was analyzed by gas chromatography to indicate that the reaction mixture comprised 89.8 wt. % of diphenyl carbonate and 9.6 wt. % of diphenyl oxalate. Therefore, the conversion ratio of diaryl oxalate was 91.5%, and the selectivity to diphenyl carbonate was 99.3%. The reaction rate (in terms of STY) for producing diaryl carbonate was 182 g/L·hr. The reaction temperatures were 250° C. in all of the chambers 2-1, 2-2, and 2-3.

Comparison Example 1

The decarbonylation reaction of diphenyl oxalate was performed under the same conditions as described in Example 1, in a reaction vessel (which had a 120 mL volume for receiving the liquid reaction mixture) illustrated in FIG. 1 but having no partitions.

When the reaction reached the steady state, the reaction mixture recovered from the reaction vessel was analyzed by gas chromatography to indicate that the reaction mixture comprised 76.6 wt. % of diphenyl carbonate and 23.1 wt. % of diphenyl oxalate. Therefore, the conversion ratio of diaryl oxalate was 79.0%, and the selectivity to diphenyl carbonate was 99.4%. The reaction rate (in terms of STY) for producing diaryl carbonate was 155 g/L·hr. The reaction temperature was 250° C.

What is claimed is:

1. A process for preparing a diaryl carbonate from a diaryl oxalate in a liquid phase by decarbonylation which utilizes a reaction vessel comprising at least two reaction chambers connected in series and comprises the steps of continuously introducing the diaryl oxalate and an organic phosphorus compound having a trivalent or pentavalent phosphorus atom and at least one carbon-phosphorus bonding into the first chamber and continuously recovering a reaction mixture comprising the diaryl carbonate from the last chamber under the condition that a mixture of the diaryl oxalate and the organic phosphorus compound is heated in the reaction chambers, while discharging carbon monoxide released from the mixture.

2. The process of claim 1, in which each of the reaction chambers has a space for receiving the carbon monoxide released from the mixture in the chamber and the spaces of the reaction chambers are connected to each other so that the carbon monoxide released in the reaction chambers can be combined and discharged together.

3. The process of claim 1, in which each of the reaction chambers has a space for receiving the carbon monoxide released from the mixture in the chamber and each of the reaction chambers has an inlet for receiving a mixture containing the diaryl oxalate and the organic phosphorus compound, an outlet for discharging the released carbon monoxide through the space, and an outlet for recovering a mixture containing the diaryl carbonate and the organic phosphorus compound.

4. The process of claim 1, wherein the organic phosphorus compound is selected from the group consisting of an organic phosphonium compound, a phosphine, a phosphine dihalide, and a phosphine oxide.

5. The process of claim 1, wherein the organic phosphorus compound is selected from the group consisting of a tetraarylphosphonium salt, a triarylphophine, a triarylphosphine dihalide and a triarylphosphine oxide.

6. The process of claim 1, wherein the organic phosphorus compound is selected from the group consisting of a tetraarylphosphonium halide and a tetraarylphosphonium hydrogen dihalide.

7. The process of claim 1, wherein an organic halide compound having a chemical structure in which a halogen atom is bonded to a carbon atom having thereon no double bond other than =O is further introduced into the first chamber.

8. The process of claim 1, wherein an inorganic halide compound selected from the group consisting of a halide of phosphorus, a halide of sulfur, a hydrogen halide, and halogen is further introduced into the first chamber.

9. The process of claim 1, wherein a chlorine-containing compound is further introduced into the first chamber.

10. A process for preparing a diaryl carbonate from a diaryl oxalate in a liquid phase by decarbonylation which utilizes a reaction vessel comprising at least two reaction chambers connected in series and comprises the steps of continuously introducing the diaryl oxalate and a decarbonylation catalyst into the first chamber and continuously recovering a reaction mixture comprising the diaryl carbonate from the last chamber under the condition that a mixture of the diaryl oxalate and the decarbonylation catalyst is heated in the reaction chambers, while discharging carbon monoxide released from the mixture.

11. The process of claim 10, in which each of the reaction chambers has a space for receiving the carbon monoxide released from the mixture in the chamber and the spaces of the reaction chambers are connected to each other so that the carbon monoxide released in the reaction chambers can be combined and discharged together.

12. The process of claim 10, in which each of the reaction chambers has a space for receiving the carbon monoxide released from the mixture in the chamber and each of the reaction chambers has an inlet for receiving a mixture containing the diaryl oxalate and the decarbonylation catalyst, an outlet for discharging the released carbon monoxide through the space, and an outlet for recovering a mixture containing the diaryl carbonate and the decarbonylation catalyst.

* * * * *